US006746607B1

(12) United States Patent
Vijayalakshmi et al.

(10) Patent No.: US 6,746,607 B1
(45) Date of Patent: Jun. 8, 2004

(54) USE OF AN ADSORBENT GEL FOR ELIMINATING AND PURIFYING BIOMOLECULES

(75) Inventors: Mookambeswaran Vijayalakshmi, Compiegne (FR); Olivier Pitiot, Soissons (FR); Cécile Legallais, Villers Sous Saint Leu (FR); Philippe Moriniere, Amiens (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/830,677

(22) PCT Filed: Oct. 28, 1999

(86) PCT No.: PCT/FR99/02635

§ 371 (c)(1),
(2), (4) Date: Jun. 4, 2001

(87) PCT Pub. No.: WO00/25911

PCT Pub. Date: May 11, 2000

(30) Foreign Application Priority Data

Oct. 30, 1998 (FR) .............................. 98 13655

(51) Int. Cl.$^7$ ..................... B01D 15/08; B01D 61/00; B01D 61/14; B01D 61/24
(52) U.S. Cl. .................. 210/656; 210/198.2; 210/252; 210/321.6; 210/635; 210/646; 210/650; 210/651; 436/73; 436/161; 436/177; 436/178; 436/528; 436/529; 530/413; 530/414; 530/417
(58) Field of Search ............. 210/198.2, 252, 210/321.6, 635, 646, 650, 651, 656; 435/2; 436/73, 161, 177, 178, 528, 529; 530/413, 414, 417

(56) References Cited

U.S. PATENT DOCUMENTS

| 4,177,038 A | 12/1979 | Biebricher et al. .......... 435/179 |
| 4,721,730 A | 1/1988 | Furuyoshi et al. .......... 210/692 |
| 4,770,774 A | 9/1988 | Ida et al. ................... 210/259 |

FOREIGN PATENT DOCUMENTS

| EP | 0 295 073 | 12/1988 |
| EP | 0 510 393 | 10/1992 |
| WO | WO 90/12803 | 11/1990 |

OTHER PUBLICATIONS

J. Porath, et al., Int. J. of Biochromatography, vol. 3, No. 1, pp. 9–17, "Adsorptive Size Exclusion Chromatography (Concentration), AdSEC", 1997.

J. Porath, et al., Nature, vol. 258, pp. 598–599, "Metal Chelate Affinity Chromatography, A New Approach to Protein Fractionation", Dec. 18, 1975.

M. Boccalatte, et al., "Amyloid Bone Disease and Highly Permeable Synthetic Membranes", The International Journal of Artificial Organs, vol. 17. No. 4, 1994, pp. 203–208.

L. Sundberg, et al., "Preparation of Adsorbents for Biospecific Affinity Chromatography", Journal of Chromatography, 90, 1974, 87–98.

U.K. Laemmli, "Cleavage of Structural Proteins During the Assembly of the Head of Bacteriophage T4", Nature, vol. 227, Aug. 15, 1970, pp. 680–685.

*Primary Examiner*—John Kim
(74) *Attorney, Agent, or Firm*—Oblon, Spivak, McClelland, Maier & Neustadt, P.C.

(57) ABSTRACT

The invention concerns the use of an adsorptive size exclusion chromatography gel, said gel essentially consisting of a polysaccharide matrix whereon is grafted a polymer coupled with an affinity ligand and having a cleavage threshold ranging between 2 kDa and 60 kDa for eliminating a purifying biomolecules.

12 Claims, 10 Drawing Sheets

USE OF AN ADSORBENT GEL FOR ELIMINATING AND PURIFYING BIOMOLECULES

Figure 1:
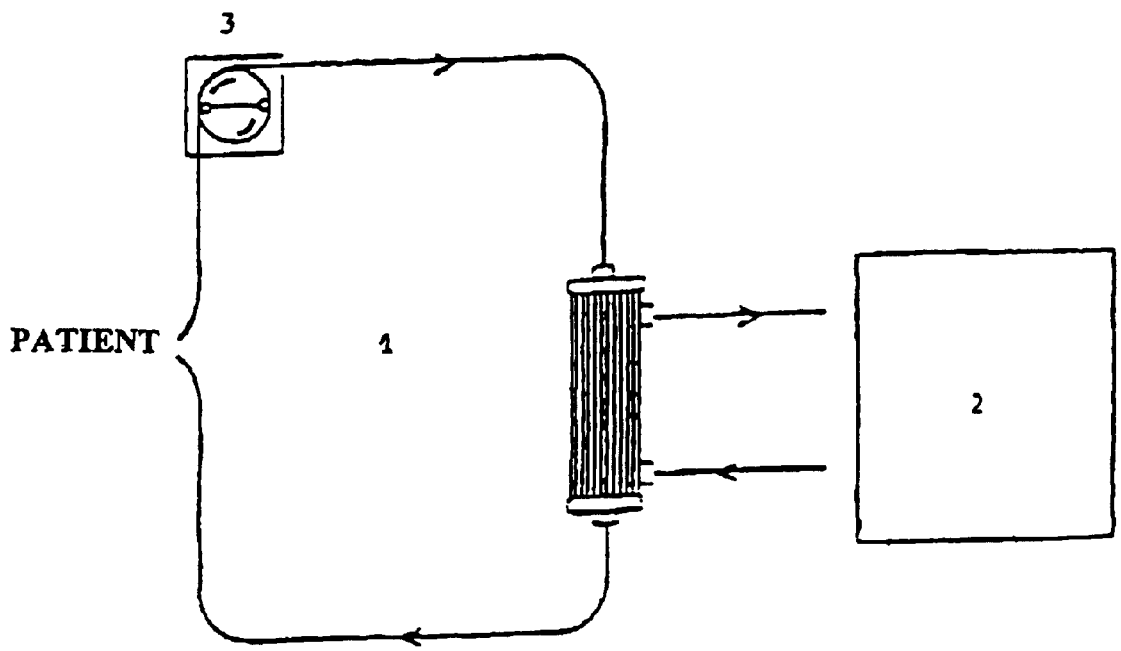

The present invention relates to the use of an adsorbent gel combining the properties of size exclusion and affinity chromatographies (AdSEC, for "Adsorptive Size Exclusion Chromatography").

The principle of an AdSEC gel results from the fusion of two chromatographic techniques: size exclusion and affinity, so as to obtain supports combining the most advantageous properties thereof.

Size exclusion chromatography (gel filtration) allows the separation of molecules according to their steric bulk alone during their passive diffusion in a molecular sieve (gel). The largest molecules cannot penetrate the crosslinked matrix and are consequently excluded more rapidly from the column. This technique possesses the characteristic feature of not exhibiting interactions between the support and the molecules, and therefore of being relatively only slightly sensitive to the biochemical conditions (pH, ionic strength) of the solution. On the other hand, because of its principle of diffusion, the limiting factors for its use are generally a long operation time (because low flow rates are used), as well as a relatively limited deposition of samples (1 to 5% of the column volume).

Affinity chromatography is based on molecular interactions between the support (matrix onto which affinity ligands are grafted) and the molecules to be separated. Among these affinity ligands, immobilized metal ions, introduced in 1975 by Porath et al. (Nature, 1975, 258, 598–599), represent a method of separation based on the interactions (coordination bonds) between biomolecules in solution and metal ions immobilized on a support; Zn(II), Cu(II), Ni(II) and Co(II) ions are the most commonly used. This is described as immobilized metal ion affinity chromatography (IMAC).

The combined use of the principles of size exclusion and affinity chromatographies (AdSEC) has been discussed by Porath et al. (Int. J. of Bio-Chromatogr., 1997, 3, 9–17). These authors have shown that iminodiacetic derivatives of dextran bearing metal ions as affinity ligand allow size exclusion and are capable of effectively concentrating solutions by their properties of adsorption and affinity. These authors have shown that an AdSEC gel column having a volume of 5 ml could bind a high percentage of compounds having a molecular weight of between 5 kDa and 50 kDa and concentrate them about 1000 fold in a single operation.

Such supports make it possible to adsorb the smallest molecules (having affinity for the grafted ligand) at high rates and volumes (not permitted in gel filtration). Moreover, during the synthesis of the adsorbent gel, the threshold of accessibility to the affinity ligand may be modulated during the synthesis of the gel according to the size of the biomolecule to be removed or to be purified.

Terminal renal insufficiency currently affects 22,000 people in France of which 20,000 are treated by iterative hemodialysis. Only 1800 can hope to undergo transplants each year, knowing that a quarter of them will return within 5 years to hemodialysis because of a rejection while waiting for a new transplant.

The survival of the uremic individual, all methods considered, can exceed 25 years if they do not suffer from a severe cardiovascular condition. In this case, the quality of survival is profoundly impaired over the years by the osteoarticular complications of terminal uremia, at the forefront of which there are described erosive arthropathies subsequent to depositions of β2-microglobulin (β2-M).

The mechanism of onset of these arthropathies begins as soon as the renal insufficiency responsible for accumulation of β2-microglobulin appears. This protein, having a molecular weight of 11,800 Da, will accumulate in the body over the years and become selectively deposited at the level of the cervical disks, of the shoulders, of the hips and of the wrists. Cardiac and digestive depositions have been reported. These depositions will make fragile the joint and the adjacent bone up to total destruction of the joint. Thus, a breakdown of the vertebral bodies is observed which can cause medullary compression with loss of control of the four members, irreversible articular luxations, loss of prehension in the hands and pseudofractures of the hip. Ductal nerve compressions are observed such as the carpal tunnel syndrome.

These complications irremediably lead the uremic individual toward invalidity and the bedridden state which conventional methods of dialysis cannot prevent. A transplant allows these lesions to be stabilized.

To effectively prevent these complications, it is important to be able to effectively purify the polluting components of blood, in particular β2-microglobulin, which are synthesized daily by the body and which are not, or not sufficiently, removed by the defective kidneys in dialyzed patients.

The purification of these various biomolecules can only be done on artificial membranes during dialysis, which are currently not sufficiently effective in spite of purification by filtration and nonspecific membrane adsorption.

The existing techniques for removing biomolecules, including β2-microglobulin, are currently of 3 types:

1. Removal of Biomolecules by Hemodialysis

Hemodialysis is a technique intended for subjects suffering from partial or complete renal insufficiency (FIG. 1). It consists in extracorporeal treatment of blood, providing the same functions as the kidney using a membrane process. The essential part of the hemodialyzer (1) is an exchange membrane, on either side of which circulate countercurrentwise the patient's blood and the dialyzate obtained from the hemodialysis generator (2). This technique allows the purification of the small molecular weight compounds polluting the blood, such as urea, amino acids, inorganic salts, which are normally removed by the kidney. In the case of serum β2-microglobulin, the various dialysis membranes commonly used possess two antagonistic properties:

capture of β2-microglobulin by nonspecific adsorption on the membrane, generation of β2-microglobulin by detachment of this molecule which is noncovalently associated with the surface of nucleated blood cells in the major histocompatibility complex type I.

The degree of generation of β2-microglobulin is one of the criteria which define the biocompatibility of the membranes. Thus, endowed with these two antagonist properties, some membranes lead overall, during a hemodialysis session, to an increase in the concentration of β2-microglobulin, whereas others reduce it.

However, regardless of the membranes used, these results level out over periods of over one year. Thus, it has been observed that the plasma level of β2-microglobulin in uremic patients after fifteen months of dialysis was invariably increased to be between 40 and 50 mg/l (against 1 to 2 mg/l in healthy patients). Such problems of biocompatibility also exist for the other biomolecules.

2. Removal of the Biomolocules by Hemofiltration

Figure 2:
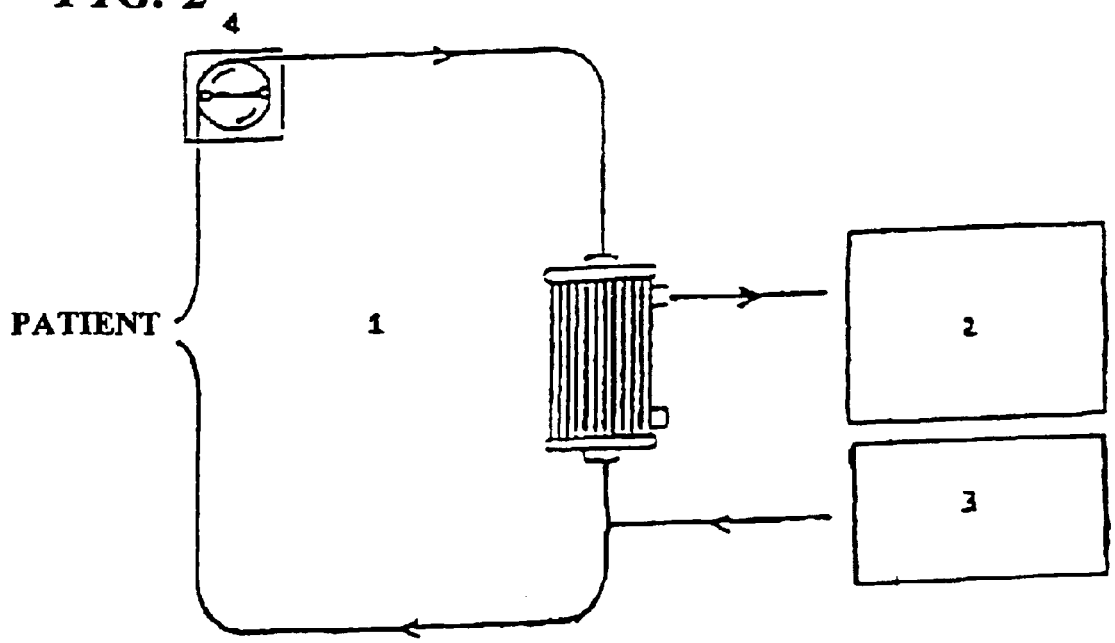

Once per month, the dialyzed individual is subjected to an ultrafiltration session. The module used (1) possesses a higher cut-off than in hemodialysis (average cut-off of 40 kDa) and allows the removal, by filtration, of the small molecules from plasma, including the smallest proteins, such as β2-microglobulin (FIG. 2). During an ultrafiltration session, the loss of plasma water is compensated by an equivalent supply of physiological saline (3).

The qualitative results, with respect to the removal of β2-microglobulin (purification and generation of this molecule by ultrafiltration membranes), are similar to those obtained in hemodialysis. There is thus a great influence of the nature of the membrane and of the duration of the hemofiltration. While some membranes appear to remove more β2-microglobulin over 5 hours (one session), a leveling out of the results is also observed over time. At the quantitative level, it appears that about 50% of the serum β2-microglobulin is removed per hemofiltration session. However, even if this technique is more effective for the purification of β2-microglobulin than hemodialysis, it remains inadequate for preventing and stopping the appearance of the disease. Furthermore, this technique has the disadvantage of removing numerous other small proteins apart from β2-microglobulin, since the ultrafiltrate is removed permanently.

3. Column/hemodialyzer Coupling

This method has been presented as an alternative to the customary hemodialysis and ultrafiltration methods (Nakazawa et al., Int. J. Artif. Organs, 1994, 17, 203–208). It consists in a serial adsorption of the biomolecules on a porous cellulose gel (350 ml of adsorbent), followed by conventional hemodialysis. In the case of β2-microglobulin, the gel is described as having a theoretical capacity for β2-microglobulin of 1 mg per ml of adsorbent. The results obtained are the best described in the literature, since in a patient in whom the initial β2-microglobulin level was 30 mg/l, this system made it possible to reduce the β2-microglobulin concentration to 10 mg/l final after 6 months of treatment. The authors presented an improvement in delaying the appearance of amyloid deposits in 2 cases out of 3, in their patients after therapy.

However, a drop in the concentration of some serum molecules (retinol binding protein, lysozymes) is also observed after treatment. This phenomenon is attributable to the direct passage of the blood through the adsorbent, which is likely to cause problems of biocompatibility.

Thus, the existing techniques for removing β2-microglobulin and other biomolecules have mainly two limits:

the biocompatibility of the supports, in particular for the generation of β2-microglobulin, that is to say the equilibrium between nonspecific adsorption on the membrane and the generation of β2-microglobulin during the passage of the cells in contact with them; this equilibrium determines the quantity of β2-microglobulin really removed during a hemodialysis or hemofiltration session.

the specificity of the substrate: indeed, the techniques of hemofiltration and of a specific binding with ligands coupled to gels lead to the undesirable removal of other molecules from serum.

A device for removing β2-microglobulin or any other biomolecule should therefore combine satisfactory (quantitative) removal with specific (qualitative) removal of the molecule in question.

In the present invention, the inventors therefore set themselves as objective:

the use, in a device intended to remove biomolecules, of an adsorbent gel combining the properties of size exclusion and affinity chromatographies, said gel essentially consisting of a polysaccharide matrix onto which is grafted a polymer coupled to an affinity ligand (AdSEC, for "Adsorptive Size Exclusion Chromatography" gel) and having an adjustable cut-off of between 2 kDa and 60 kDa, the use of an AdSEC gel for separating and purifying biomolecules having a molecular weight of between 2 kDa and 60 kDa, a device intended for the removal of biomolecules having a molecular weight of between 2 kDa and 60 kDa comprising an ultrafiltration module optionally upstream and in series with a dialysis module and using an AdSEC gel column having an adjustable cut-off of between 2 kDa and 60 kDa, said column being mounted branching off from said ultrafiltration module; this device makes it possible to dispense with the problems of biocompatibility and to specifically remove the desired biomolecules, a device for purifying biomolecules having a weight of between 2 kDa and 60 kDa using an AdSEC gel column having an adjustable cut-off of between 2 kDa and 60 kDa, said column optionally branching off from a filtration system; this device makes it possible to separate normal biomolecules and biomolecules modified for example by glycation.

In one advantageous embodiment, the polysaccharide matrix is agarose or is based on an agarose derivative, the polymer may be polyethylene glycol (PEG) or polypropylene glycol (PPG) and the affinity ligand may be, for example, a metal-chelating agent coupled to metal ions, a protein, a peptide, an enzyme substrate or an enzyme inhibitor.

In a preferred embodiment, the adsorbent gel consists of a matrix based on an agarose derivative onto which is grafted polyethylene glycol coupled to iminodiacetic acid (IDA) itself coupled to metal ions, for example copper(I) ions; this complex is called IMAdSEC ("Immobilized Metal ion Adsorptive Size Exclusion Chromatography") gel.

In an also preferred embodiment, the cut-off of the adsorbent gel is 20 kDa, thus allowing the removal or the purification of biomolecules whose molecular weight is less than 20 kDa, in particular serum β2-microglobulin.

The purification system according to the present invention possesses the characteristic feature of placing the adsorbent gel for the biomolecule to be removed branching from the circulation system for purifying. Thus, when blood is purified, there is at no time contact between the gel and the formed elements of the blood, therefore the problems of biocompatibility (for example generation of β2-microglobulin through contact with the nucleated cells of the blood) or hemolysis of the cells in contact with the gel are avoided.

Furthermore, unlike the other techniques currently used, the purification of the biomolecule to be removed or to be purified is carried out using a ligand which will retain only this molecule. This specificity is obtained by virtue of the double sieving of the ultrafiltration membrane (which retains for example the formed elements of the blood and the large serum molecules) and of the AdSEC gel which prevents access to the ligand for other molecules with affinity for the affinity ligand but whose size is greater than the cut-off of the gel.

The other advantage of the use of this AdSEC gel is its ease of regeneration. For example, when a metal is used as affinity ligand, it may be chelated by a solution of EDTA, which makes it possible to detach any molecule adsorbed onto the gel, thus allowing cleaning of the gel, its regeneration with a new metal load and its sterilization.

The removal system according to the invention may be used for example in the context of kidney dialysis; in this case, there is an additional advantage linked to the fact that the fraction purified by passage over the AdSEC gel returns to the patient, thus limiting losses of other elements present in the blood.

Figure 3A:
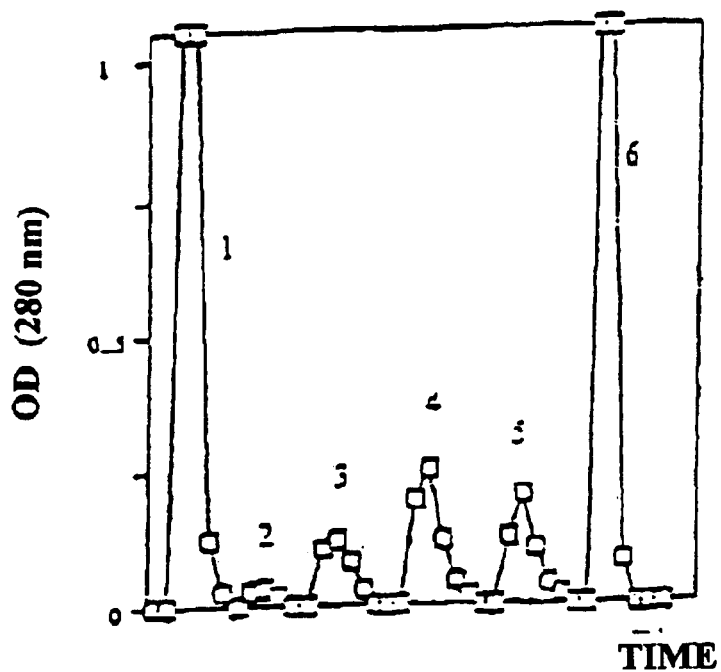
Figure 3B:
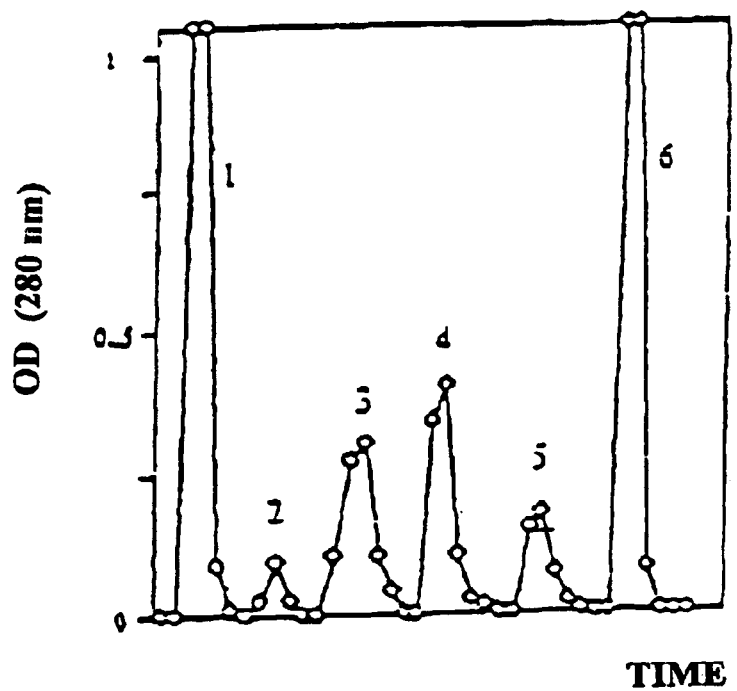
Figure 3C:
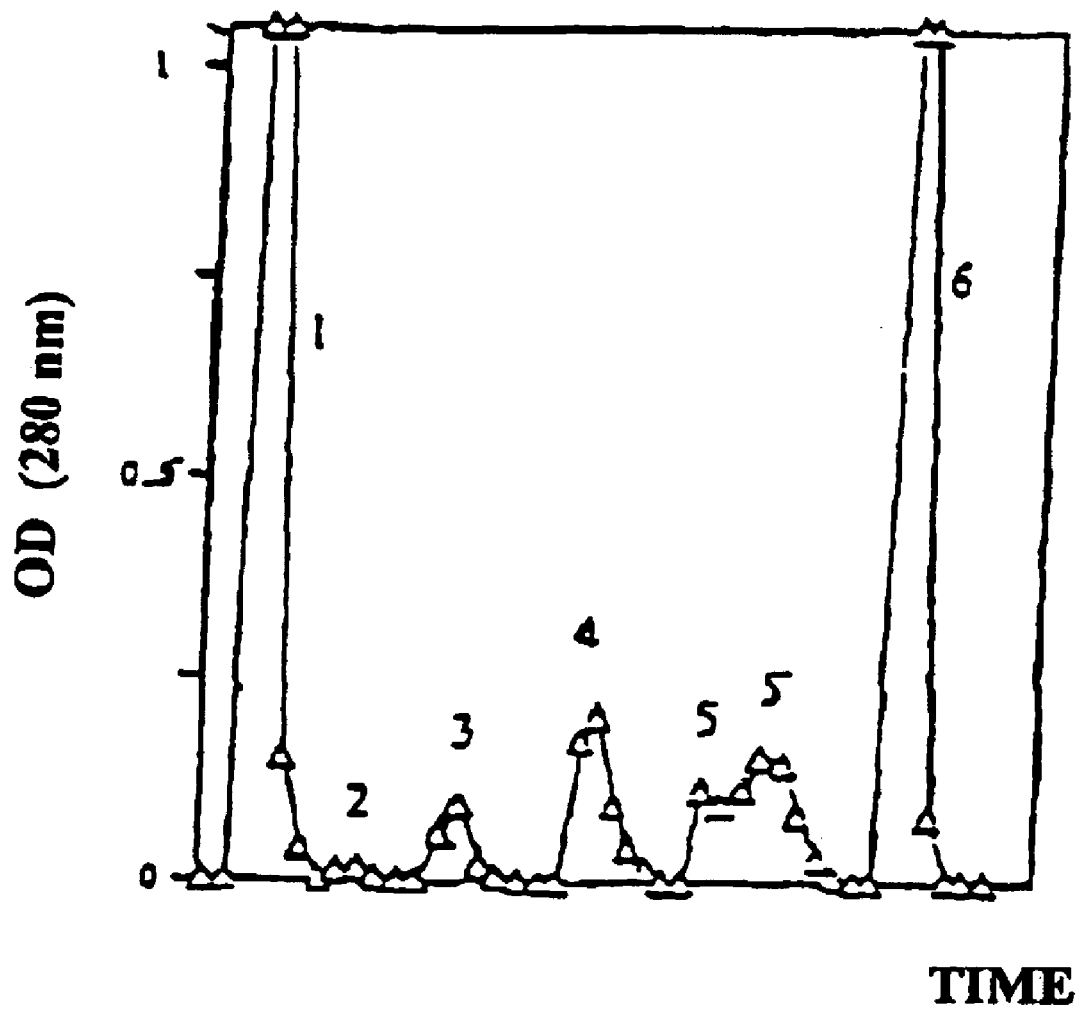
Figure 6:
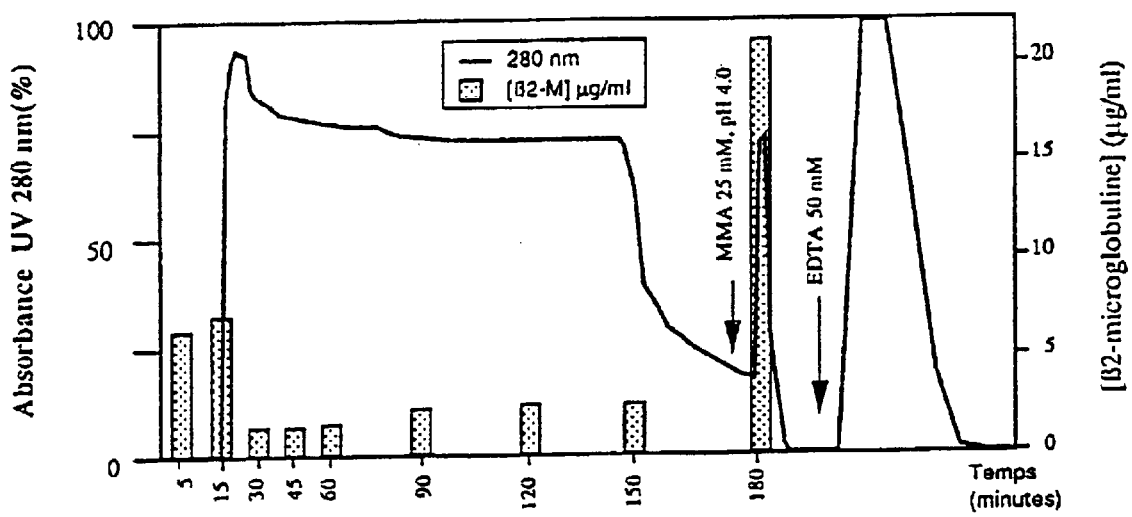
Figure 7:
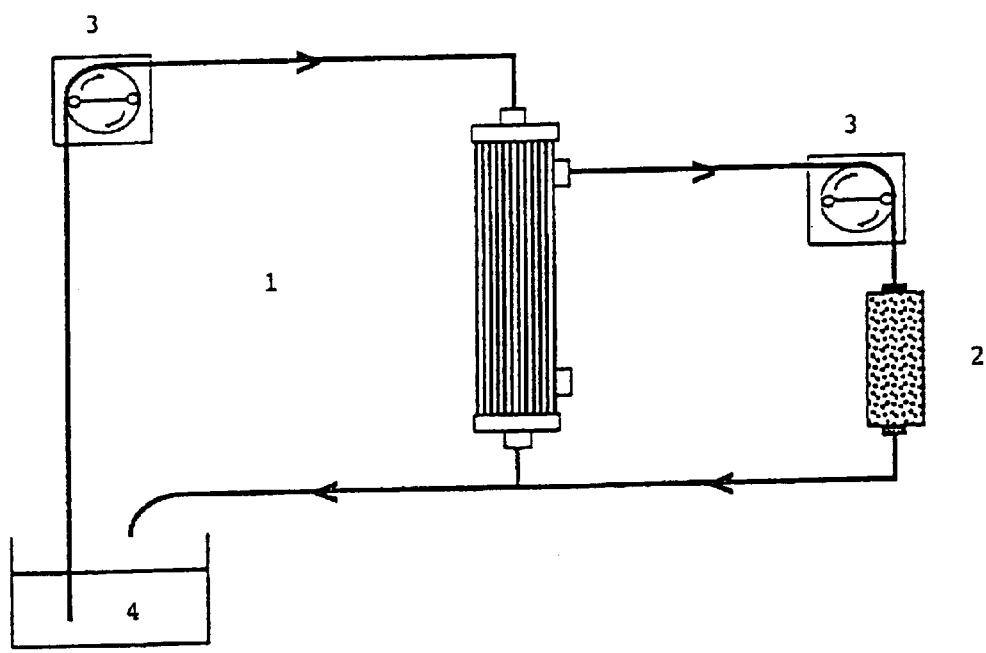
Figure 8:
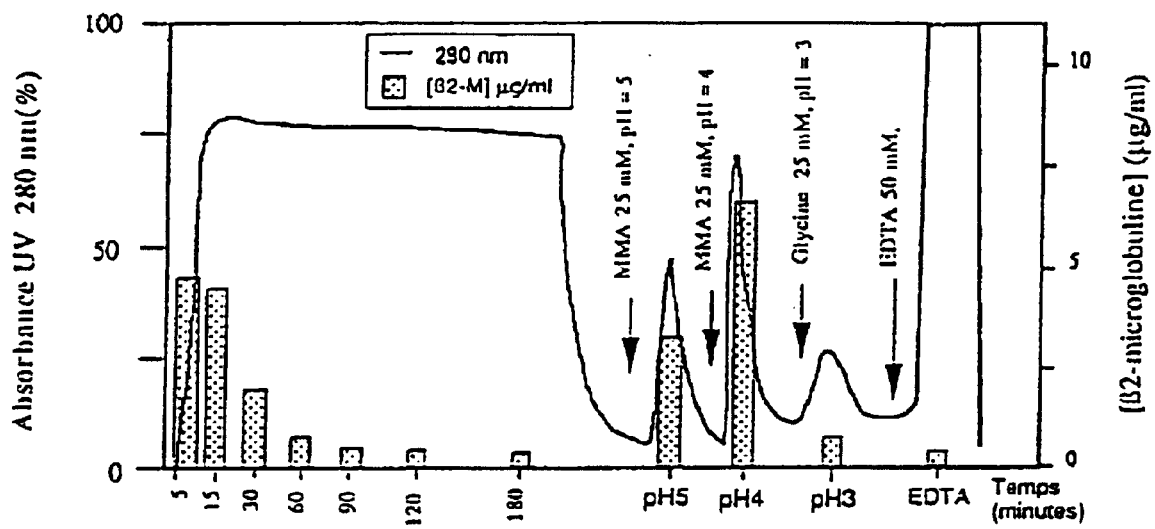
Figure 9:
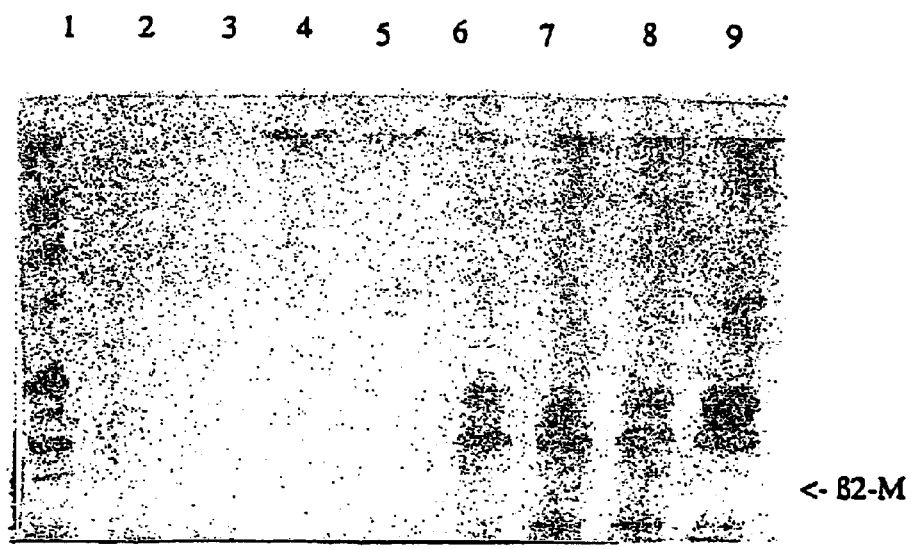
Figure 10:
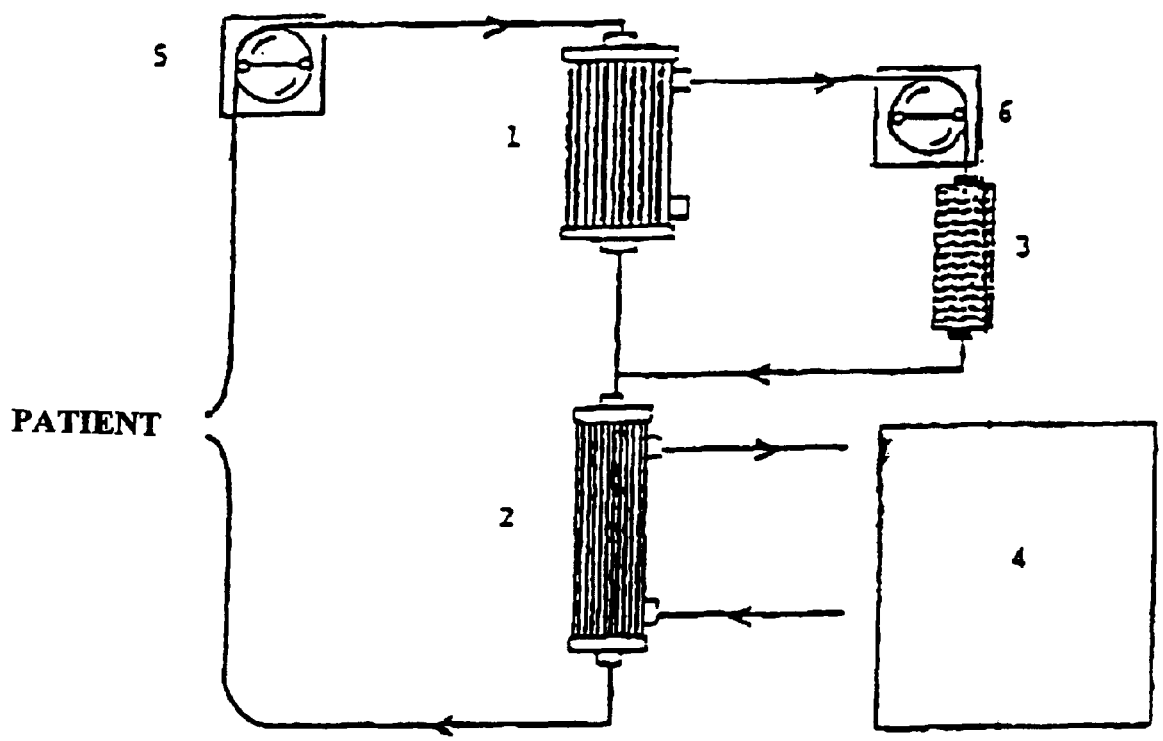

In addition to the preceding features, the invention further comprises other features which will emerge from the description which follows, which refers to examples as well as to the appended figures in which:

FIG. 1 represents the general diagram for renal dialysis; (1) hemodialyzer, (2) hemodialysis generator, (3) pump, FIG. 2 represents the diagram for a hemofiltration by ultrafiltration; (1) hemofilter, (2) hemodialysis generator, (3) physiological saline, (4) pump, FIG. 3 illustrates the chromatographies on metal ions (copper) immobilized on 3 types of gels: A Sépharose® 4B-IDA-copper, peak 1: nonadsorbed proteins; peak 2: elution at pH 6.0; peak 3: elution at pH 5.0; peak 4: elution at 4.0; peak 5: elution at pH 3.0; peak 6: 25 mM EDTA. B Novarose®-IDA-copper, peak 1: nonadsorbed proteins; peak 2: elution at pH 6.0; peak 3: elution at pH 5.0; peak 4: elution at pH 4.0; peak 5: elution at pH 3.0; peak 6: 25 mM EDTA. C Novarose®-PEG/IDA-copper (IMAdSEC), peak 1: nonadsorbed proteins; peak 2: elution at pH 6.0; peak 3: elution at pH 5.0; peak 4: elution at pH 4.0; peak 5: elution at pH 3.0 (1st peak); peak 5' elution at pH 3.0 (2nd peak); peak 6: 25 mM EDTA, FIG. 4 illustrates the electrophoretic analysis of the fractions separated by chromatography illustrated in FIG. 3; the numbers correspond to the fractions separated by chromatography in FIG. 3; A Sépharose® 4B-IDA-copper. B Novarose®-IDA-copper. C Novarose®-PEG/IDA-copper (IMAdSEC). This figure illustrates the specificity of the IMAdSEC gel for β2-microglobulin relative to the two other types of gel, FIG. 5 illustrates the analysis by mass spectrometry of the protein composition of the starting ultrafiltrate and of the fraction retained on IMAdSEC gel. A (I) spectrum for the ultrafiltrate, (II) deconvolution of the spectrum (a) calculation of the mass of β2-microglobulin (b) calculation of the mass of albumin. B (I) spectrum for the purified fraction, (II) deconvolution of the spectrum and calculation of the mass of β2-microglobulin, FIG. 6 illustrates the capacity of the IMAdSEC gel for β2-microglobulin, FIG. 7 illustrates the mounting, on a branch, of a filtration module of the purification device according to the invention; (1) ultrafiltration module, (2) column containing the IMAdSEC gel, (3) pumps, (4) ultrafiltrate, FIG. 8 illustrates the capacity of the device illustrated in FIG. 7 for the removal of β2-microglobulin from an ultrafiltrate of a uremic patient, FIG. 9 illustrates the electrophoretic analysis of the fractions separated by chromatography illustrated in FIG. 8; 1: ultrafiltrate; 2: 15 minutes of passage over the IMAdSEC gel; 3: 30 minutes of passage over the IMAdSEC gel; 4: 120 minutes of passage over the IMAdSEC gel; 5: fraction eluted at pH 5.0; 6: fraction eluted at pH 4.0; 7 fraction eluted at pH 3.0; 8: fraction eluted with EDTA, 9: protein standard, FIG. 10 represents a hemodialysis system comprising the device according to the invention; (1) hemofilter, (2) hemodialyzer, (3) IMAdSEC column, (4) hemodialysis generator, (5) blood pump and (6) ultrafiltration pump.

EXAMPLE 1

Determination of the Specificity and of the Capacity of an IMAdSEC Gel: (Novarose®-PEG/IDA-copper) for β2-microglobulin 1. Synthesis of the Novarose®-PEG/IDA-copper Gel:

Step 1: coupling of PEG and creation of the cut-off of the gel:

10 g of Novarose® Act High 100/40 (INOVATA, Bromma, Sweden), previously dried by suction, are taken up in 5 ml of 1 M $Na_2CO_3$, pH>12 and 5 ml of deionized water. 5 ml of 1 M $Na_2CO_3$, pH>12, 5 ml of deionized water and 30 ml of $NH_2$-PEG-$NH_2$ at 10% in 1 M $Na_2CO_3$, pH>12, are added. The mixture is left under gentle stirring at room temperature (22° C.) for 1 to 24 hours depending on the desired cut-off (this time is 4 hours for a cut-off of 20 kDa which is the desired cut-off for β2-microglobulin).

Step 2: coupling of the ligand:iminodiacetic acid (IDA).

The gel obtained in step 1 is rinsed on sintered material (by suction) with a solution of deionized water. It is resuspended in a solution comprising 15 ml of 1 M $Na_2CO_3$, pH>12, 15 ml of deionized water, and 10 ml of a solution of IDA at 10% in 1 M $Na_2CO_3$, pH>12. The mixture is left under gentle stirring at room temperature (22° C.) for 48 hours. The IMAdSEC gel is rinsed on sintered material successively with deionized water, with a 1 M solution of sodium hydroxide, with deionized water, with a 0.1M solution of hydrochloric acid, and then with deionized water. The gel thus obtained is kept at 4° C. in a solution of 20% ethanol until it is used.

Step 3: coupling of the metal ions (copper Cu II ions):

The metal load is prepared using an aqueous solution of copper sulfate at 50 mM under conventional conditions.

2. Preparation of the Biological Solutions

The products are derived from the hemofiltration of blood during an ultrafiltration session in the context of the treatment of uremic patients (FIG. 2). Ultrafiltrates (pH 7.2, 13 mS/cm) are used whose β2-microglobulin concentration varies from 7 to 20 mg/l according to the patients.

3. Specificity of the Novarose®-PEG/IDA-copper Gel for β2-microglobulin Compared with Gels without Sieving Sépharose® 4B-IDA-copper and Novarose®-IDA-copper Procedure:

3 gels were tested: Sépharose® 4B-IDA-copper, Novarose®-IDA-copper (IMAC gels), and Novarose®-PEG/IDA-copper (IMAdSEC gel), for their capacity to adsorb the molecules of the ultrafiltrate from a uremic patient. The Sépharose® 4B-IDA gel was prepared according to the protocol described by Sundberg and Porath (J. Chromatogr., 1974, 90, 87–98). The Novarose®-IDA gel results from the same protocol as that described above at point 1 for the synthesis of the IMAdSEC gel, where only the second and the third steps were carried out (no prior activation of the gel with PEG). 2 ml of gel are applied to a column (diameter 1 cm) and low-pressure chromatography (1 ml/min) is carried out. 10 ml of ultrafiltrate from a patient, whose β2-microglobulin concentration is 20 µg/ml, are passed over each of the 3 different gels in closed circuit for 20 minutes. The equilibration and the rinsing of each column after adsorption of the ultrafiltrate are performed with an MMA buffer of pH 7.0 (MMA=MOPS, MES, Acetate, 25 mM each). The elution is carried out with a discontinuous decreasing pH gradient (buffer, 25 mM MMA, pH 6.0, then pH 5.0, then pH 4.0 and 25 mM glycine at pH 3.0), and then with a solution of EDTA (50 mM) to detach the copper. The protein content is measured during the chromatography by reading the optical density ($\lambda$=280 nm) with a detector placed at the outlet of the column. The assay of β2-microglobulin is carried out by an immunological assay (rabbit polyclonal antibody anti-human β2-microglobulin, Dako, Denmark) using a nephelometry apparatus (Beckman, USA). The various fractions are analyzed by SDS-PAGE electrophoresis, according to the protocol described by Laemmli (Nature, 1970, 227, 680–685), and staining of the proteins with silver nitrate. After desalting and concentration, the fractions are analyzed by mass spectrometry (ESI-MS for "ElectroSpray Ionisation Mass Spectrometry" technique), whose sensitivity, determining the mass to the nearest dalton, makes it possible to identify the molecules.

Figure 4A:
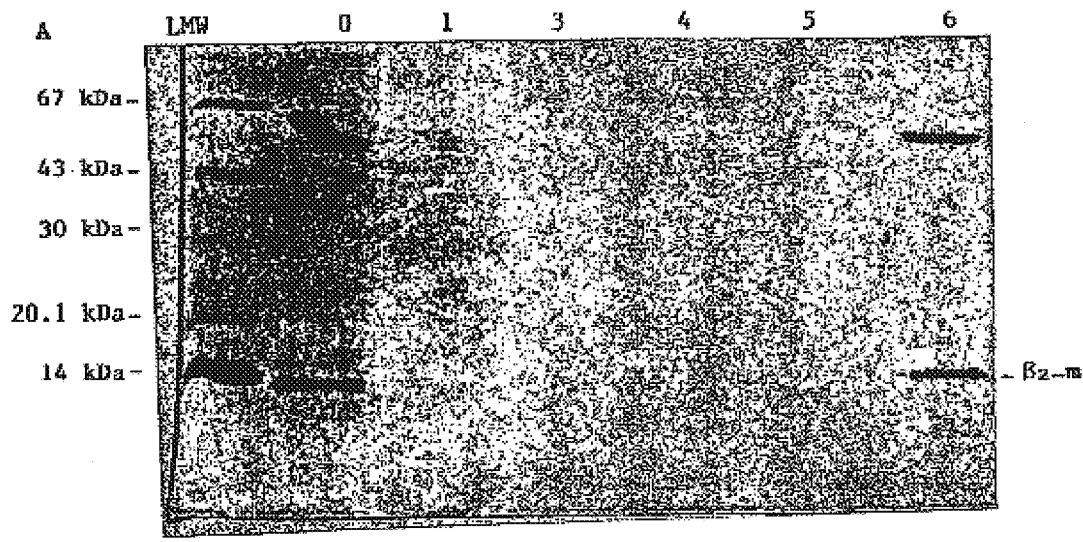

Results:

The chromatography on Sépharosee® 4B-IDA-copper gel (FIG. 3a) shows that, while the β2-microglobulin has a high affinity for the chelated copper, its elution occurs in the same fractions as the albumin (FIG. 4A). All the proteins of the ultrafiltrate are adsorbed onto the gel, which therefore exhibits no specificity for β2-microglobulin.

Figure 4B:
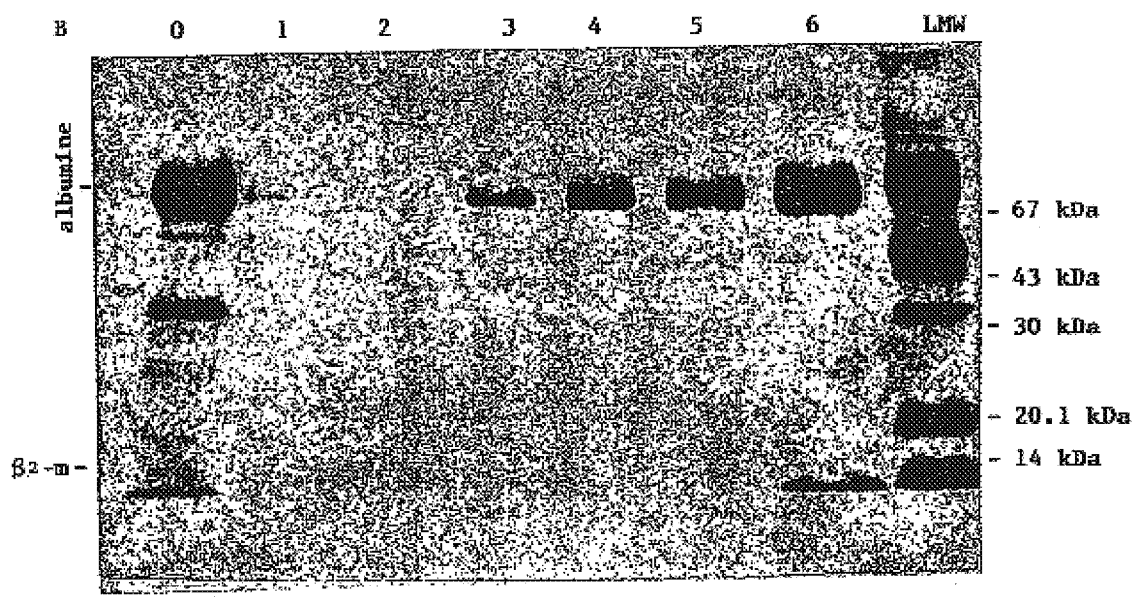

The chromatography on Novarose®-IDA-copper gel (FIG. 3B) also shows that this type of gel allows the adsorption of all the proteins of the ultrafiltrate (FIG. 4B). Its capacity in relation to copper which is lower than that of Sépharose®-4B-IDA results, on the other hand, in elutions of proteins during the discontinuous pH gradient, unlike the Sépharose® 4B-IDA gel (FIG. 4B versus 4A). Like the latter, it does not offer specificity for β2-microglobulin (FIG. 4B).

Figure 4C:
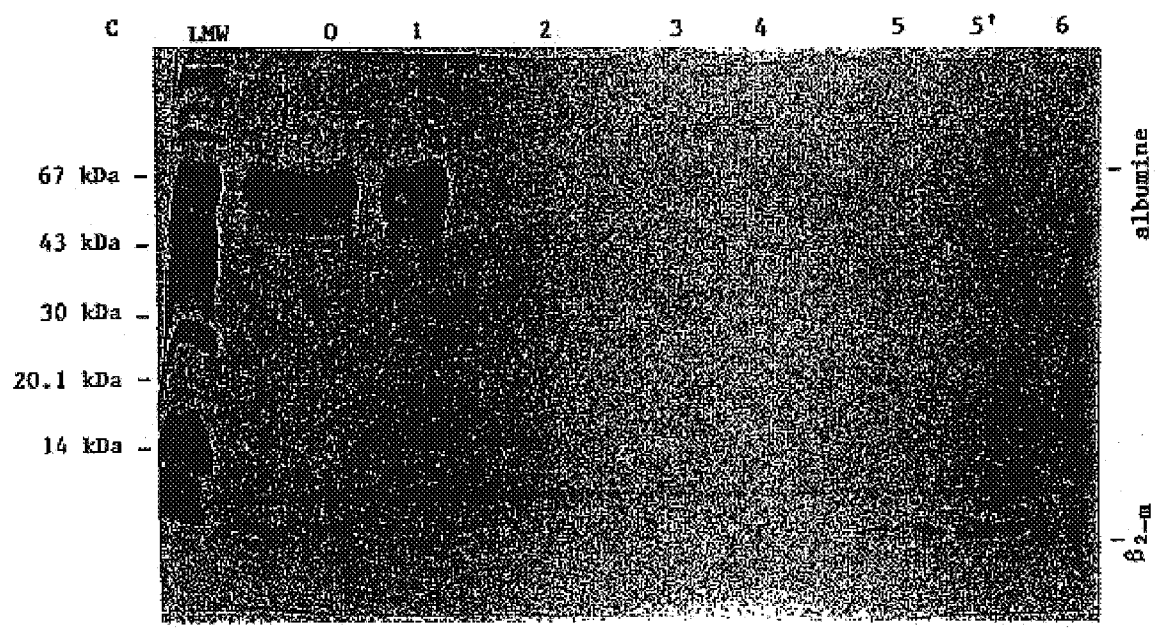

The chromatography on Novarose®-PEG/IDA-copper gel, on the other hand, allowed the adsorption of solely the β2-microglobulin of the ultrafiltrate from the patient. Its elution takes place at pH 3.0 as two distinct peaks (FIG. 4C).

In the three types of chromatography, the analyses by nephelometry confirm the complete disappearance of β2-microglobulin from the ultrafiltrate fraction passed over the 3 types of gel and its elution from the column.

Figure 5A:
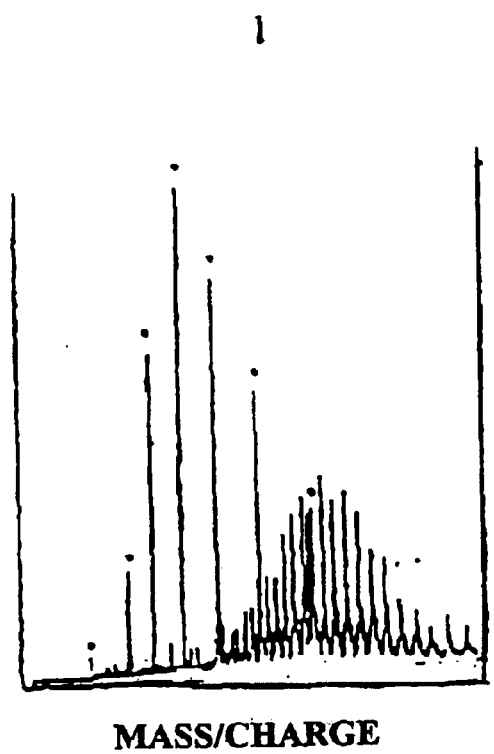
Figure 5A:
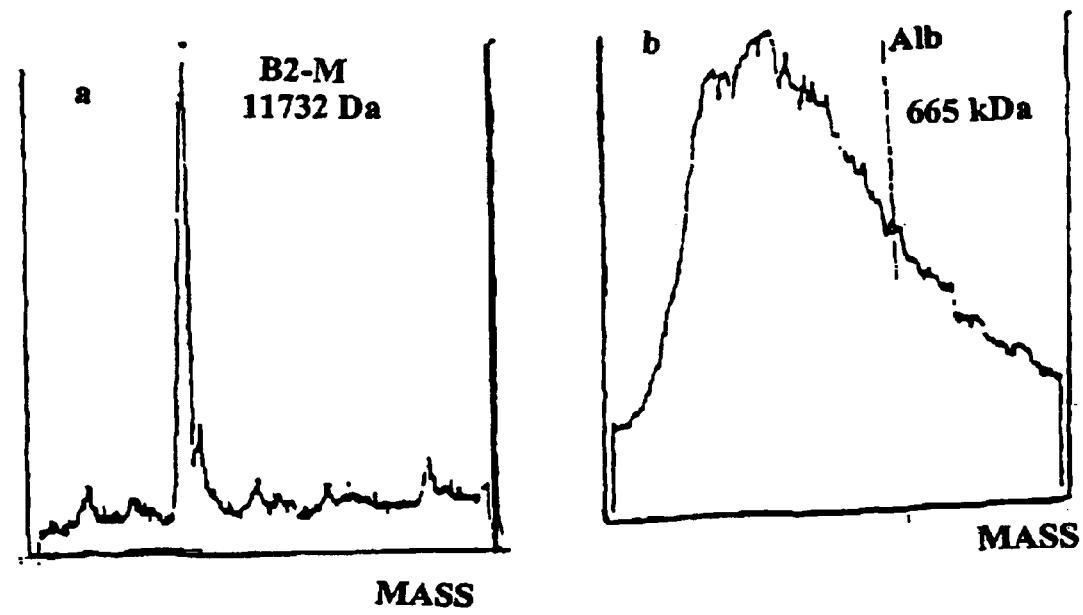
Figure 5B:
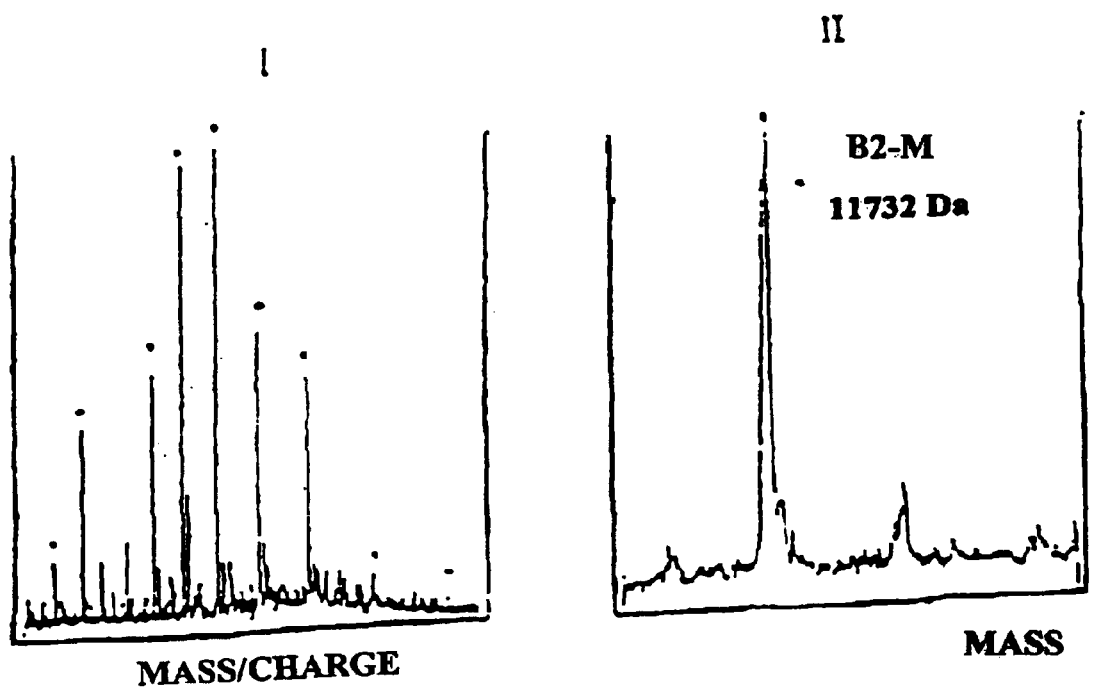

ESI-MS analysis shows that the chromatography on IMAdSEC gel makes it possible to pass from a fraction consisting of a starting mixture: albumin+β2-microglobulin, to a fraction eluted at pH 3.0 which contains only β2-microglobulin (FIG. 5A versus 5B).

These results show the affinity of β2-microglobulin for the ligand (chelated metal, here copper) and the specificity offered by the molecular sieving (coupling of PEG) of the IMAdSEC gel compared with the conventional IMAC gels.

4. Capacity of the IMAdSEC-copper gel for β2-microglobulin

Procedure:

50 ml of ultrafiltrate from a uremic patient, containing 350 μg of β2-microglobulin (that is a β2-microglobulin concentration of 7 μg/ml) circulates in closed circuit for 150 minutes on 0.65 ml of IMAdSEC gel under the same chromatographic conditions as above (flow rate=1 ml/min). The elution is carried out directly at pH 4.0 (FIG. 6).

Results:

After 150 minutes, the β2-microglobulin concentration measured by nephelometry is 2.3 μg/ml, that is a remaining β2-microglobulin quantity of 115 μg. Consequently, 235 μg of β2-microglobulin were bound to the 0.65 ml of gel, which corresponds to a binding capacity of the IMAdSEC-copper gel of 360 μg/ml. SDS-PAGE and ESI-MS analysis of the fractions was carried out as described above. The quantity of β2-microglobulin, eluted at pH 4.0, is about 180 μg instead of 235 μg expected. The difference may be explained by the absence of measurement of the rinsing and EDTA fractions which are also likely to contain β2-microglobulin.

These results suggest that, taking into account these performances and this specificity for β2-microglobulin, a column of 500 to 750 ml of IMAdSEC-copper gel would make it possible to remove 250 mg of β2-microglobulin, a quantity which corresponds to 5 liters of blood at a β2-microglobulin concentration of 50 mg/l.

EXAMPLE 2

Separation and Purification of β2-microglobulin by a Device Comprising the Coupling of an Ultrafiltration Module and an IMAdSEC Column Procedure The assembly represented in FIG. 7 is used. The ultrafiltration module (1) used is composed of 100 Polysulfone hollow fibers drawn from a commercial ultrafiltration module model Fresenius F80.

50 ml of ultrafiltrate from a uremic patient (β2-microglobulin concentration=7 μg/ml) are passed in a closed circuit for 3 hours on the ultrafiltration/column of IMAdSEC gel (0.65 ml of IMAdSEC gel) minimodule assembly. The chromatography conditions are those of Example 1, namely: buffer, 25 mM MMA, pH 6.0, then pH 5.0, then pH 4.0 and 25 mM glycine at pH 3.0, then 50 mM EDTA to elute the copper chelated on the gel.

After 3 hours, the β2-microglobulin concentration in the reservoir is measured by nephelometry.

Results

The concentration passes from 7 μg/ml of β2-microglobulin (that is a starting quantity of 350 μg) to about 1 μg/ml (50 μg of β2-microglobulin remaining). Consequently, about 300 μg of β2-microglobulin were bound to the 0.65 ml of IMAdSEC gel, which corresponds to a binding capacity of the IMAdSEC gel for β2-microglobulin of 461 μg/ml.

ESI-MS (FIG. 8) and SDS-PAGE (FIG. 9) analysis of the fractions show that the β2-microglobulin was adsorbed specifically by the IMAdSEC gel. It is eluted as two main fractions at pH 4.0 and pH 5.0.

These results suggest that the IMAdSEC gel could be useful for the separation of biomolecules and their isoforms such as for example normal β2-microglobulin and glycated β2-microglobulin.

What is claimed is:

1. A device for removing biomolecules comprising an ultrafiltration module optionally upstream and in series with a dialysis module, wherein this device further comprises a column containing an adsorbent gel combining the properties of size exclusion and affinity chromatographies, said adsorbent gel consisting essentially of a polysaccharide matrix onto which is grafted a polymer coupled to an affinity ligand and having an adjustable cut-off of between 2 kDa and 60 kDa, said column being mounted branching from said ultrafiltration module.

2. The device according to claim 1, wherein the adsorbent gel consists of a matrix based on an agarose derivative onto which is grafted polyethylene glycol coupled to iminodiacetic acid itself coupled to copper(I) ions and having a cut-off of 20 kDa.

3. The device according to claim 2, wherein the biomolecule is serum β2-microglobulin.

4. The device according to claim 1, wherein the device is an extracorporeal dialysis system.

5. A method for removing biomolecules from blood, said method comprising passing said blood in a device according to claim 1.

6. The method according to claim 5, wherein the device comprises an adsorbent gel consisting of a matrix based on an agarose derivative onto which is grafted polyethylene glycol coupled to iminodiacetic acid itself coupled to copper (I) ions and having a cut-off of 20 kDa.

7. The method according to claim 5, wherein the biomolecule is serum β2-microglobulin.

8. The method according to claim 5, wherein the device is an extracorporeal dialysis system.

9. A device for separating and purifying biomolecules comprising a column containing an adsorbent gel combining the properties of size exclusion and affinity chromatographies, said gel consisting essentially of a polysaccharide matrix onto which is grafted a polymer coupled to an affinity ligand and having an adjustable cut-off of between 2 kDa and 60 kDa, said column being mounted branching from a ultrafiltration module.

10. The device according to claim 9, wherein the adsorbent gel consists of a matrix based on an agarose derivative onto which is grafted polyethylene glycol coupled to iminodiacetic acid itself coupled to copper(I) ions and having a cut-off of 20 kDa.

11. The device according to claim 10, wherein the biomolecule is serum β2-microglobulin.

12. The device according to claim 9, wherein the device is an extracorporeal dialysis system.

* * * * *